United States Patent
Hori

(10) Patent No.: US 11,660,039 B2
(45) Date of Patent: May 30, 2023

(54) MEASUREMENT PROBE FOR PRESCHOOLERS AND BRAIN FUNCTION MEASURING DEVICE FOR PRESCHOOLERS

(71) Applicant: SHIMADZU CORPORATION, Kyoto (JP)

(72) Inventor: Ayaka Hori, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 574 days.

(21) Appl. No.: 16/790,844

(22) Filed: Feb. 14, 2020

(65) Prior Publication Data

US 2020/0305782 A1 Oct. 1, 2020

(30) Foreign Application Priority Data

Mar. 28, 2019 (JP) .............................. JP2019-062366

(51) Int. Cl.
*A61B 5/00* (2006.01)
*A61B 5/1455* (2006.01)

(52) U.S. Cl.
CPC .......... *A61B 5/4064* (2013.01); *A61B 5/0082* (2013.01); *A61B 5/6814* (2013.01); *A61B 2503/06* (2013.01)

(58) Field of Classification Search
CPC ... A61B 5/4064; A61B 5/0059; A61B 5/0075; A61B 5/0082; A61B 5/1455; A61B 5/14551; A61B 5/14552; A61B 5/14553; A61B 5/6814; A61B 5/6803; A61B 2562/0233
See application file for complete search history.

(56) References Cited

U.S. PATENT DOCUMENTS

| | | | |
|---|---|---|---|
| 7,039,454 B1 | 5/2006 | Kaga et al. | |
| 8,412,298 B2 * | 4/2013 | Ninomiya | A61B 5/6814 600/344 |
| 2009/0054789 A1 | 2/2009 | Kiguchi et al. | |

FOREIGN PATENT DOCUMENTS

| | | |
|---|---|---|
| CN | 101371780 A | 2/2009 |
| JP | 2008-289710 A | 12/2008 |
| JP | 2008-307318 A | 12/2008 |
| JP | 2009-45281 A | 3/2009 |
| JP | 2015-33561 A | 2/2015 |

OTHER PUBLICATIONS

Communication dated Jul. 22, 2021 from the Korean Intellectual Property Office in Application No. 10-2020-0010476.
Office Action dated May 17, 2022 from the China National Intellectual Property Administration in CN Application No. 202010123190.1.
Communication dated Dec. 21, 2021 from the Chinese Patent Office in Chinese Application No. 202010123190.1.
Notice of Reasons for Refusal dated May 31, 2022 from the Japanese Patent Office in Japanese Application No. 2019-062366.

* cited by examiner

*Primary Examiner* — Chu Chuan Liu
(74) *Attorney, Agent, or Firm* — Sughrue Mion, PLLC

(57) ABSTRACT

A measurement probe for preschoolers includes a fiber configured to irradiate a head of a subject with light, and a holder made of a metal or resin other than rubber. A tip surface of a tip of the fiber that contacts the head of the subject is flat, and a corner of a tip surface of the holder that contacts the head of the subject is chamfered.

6 Claims, 5 Drawing Sheets

MEASUREMENT PROBE FOR PRESCHOOLERS AND BRAIN FUNCTION MEASURING DEVICE FOR PRESCHOOLERS

CROSS-REFERENCE TO RELATED APPLICATIONS

This application claims the benefit of priority to Japanese Patent Application No. 2019-062366 filed on Mar. 28, 2019. The entire contents of this application are hereby incorporated herein by reference.

BACKGROUND OF THE INVENTION

Field of the Invention

The present invention relates to a measurement probe for preschoolers and a brain function measuring device for preschoolers, and more particularly, it relates to a measurement probe for preschoolers and a brain function measuring device for preschoolers disposed in contact with the head of a preschooler during brain function measurement.

Description of the Background Art

Conventionally, a configuration in which a plurality of measurement probes are placed on the head of a subject during brain function measurement is known. Such a configuration is disclosed in Japanese Patent Laid-Open No. 2008-307318, for example.

Japanese Patent Laid-Open No. 2008-307318 discloses a biophotonic measurement device including a holder attached to the head of a subject and a plurality of probes attached to the holder. The biophotonic measurement device disclosed in Japanese Patent Laid-Open No. 2008-307318 disperses the pressure on the scalp of the subject by attaching rubber pads to the tips of optical fibers of the probes such that the pain of the subject at the time of wearing the biophotonic measurement device is alleviated. Although not specified in Japanese Patent Laid-Open No. 2008-307318, a predetermined number or more of (relatively many) probes are required to accurately measure the brain function of the subject using the biophotonic measurement device.

When the biophotonic measurement device is used for preschoolers with small heads, it is necessary to reduce the size of the holder according to the size of the head without reducing the number of probes in order to maintain the measurement accuracy. However, when the size of the holder is reduced, a space between the probes becomes smaller, and the rubber pads cannot be attached to the probes. Therefore, the head may be painful at the time of wearing the biophotonic measurement device.

SUMMARY OF THE INVENTION

The present invention is intended to solve the above problem. The present invention aims to provide a measurement probe for preschoolers and a brain function measuring device for preschoolers capable of alleviating the pain at the time of attaching the measurement probe for preschoolers without providing rubber pads.

In order to attain the aforementioned object, a measurement probe for preschoolers according to a first aspect of the present invention is a measurement probe for preschoolers for brain function measurement disposed in contact with a head of a subject, and includes a fiber configured to irradiate the head of the subject with light, and a holder provided on the fiber so as to cover an outer peripheral surface of a tip of the fiber, the holder being made of a metal or resin other than rubber. A tip surface of the tip of the fiber that contacts the head of the subject is flat, and a corner of a tip surface of the holder that contacts the head of the subject is chamfered.

In order to attain the aforementioned object, a brain function measuring device for preschoolers according to a second aspect of the present invention includes a device main body, a plurality of measurement probes for preschoolers electrically connected to the device main body, and a holder attached with the plurality of measurement probes for preschoolers, the holder being configured to maintain a state in which the plurality of measurement probes for preschoolers are connected to a head of a subject. The plurality of measurement probes for preschoolers each include a fiber configured to irradiate the head of the subject with light, and a holder provided on the fiber so as to cover an outer peripheral surface of a tip of the fiber, the holder being made of a metal or resin other than rubber, a tip surface of the tip of the fiber that contacts the head of the subject is flat, and a corner of a tip surface of the holder that contacts the head of the subject is chamfered.

According to the present invention, as described above, the measurement probe for preschoolers for brain function measurement disposed in contact with the head of the subject includes the fiber configured to irradiate the head of the subject with light and the holder provided on the fiber so as to cover the outer peripheral surface of the tip of the fiber and made of the metal or resin other than rubber, and the corner of the tip surface of the holder that contacts the head of the subject is chamfered. Accordingly, the corner of the tip surface, which contacts the head of the subject, of the holder made of the metal or resin other than rubber and configured to cover the outer peripheral surface of the tip of the fiber is chamfered such that a pressure applied to the head is reduced, and thus the pain at the time of attaching the measurement probe for preschoolers can be alleviated without providing rubber pads.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
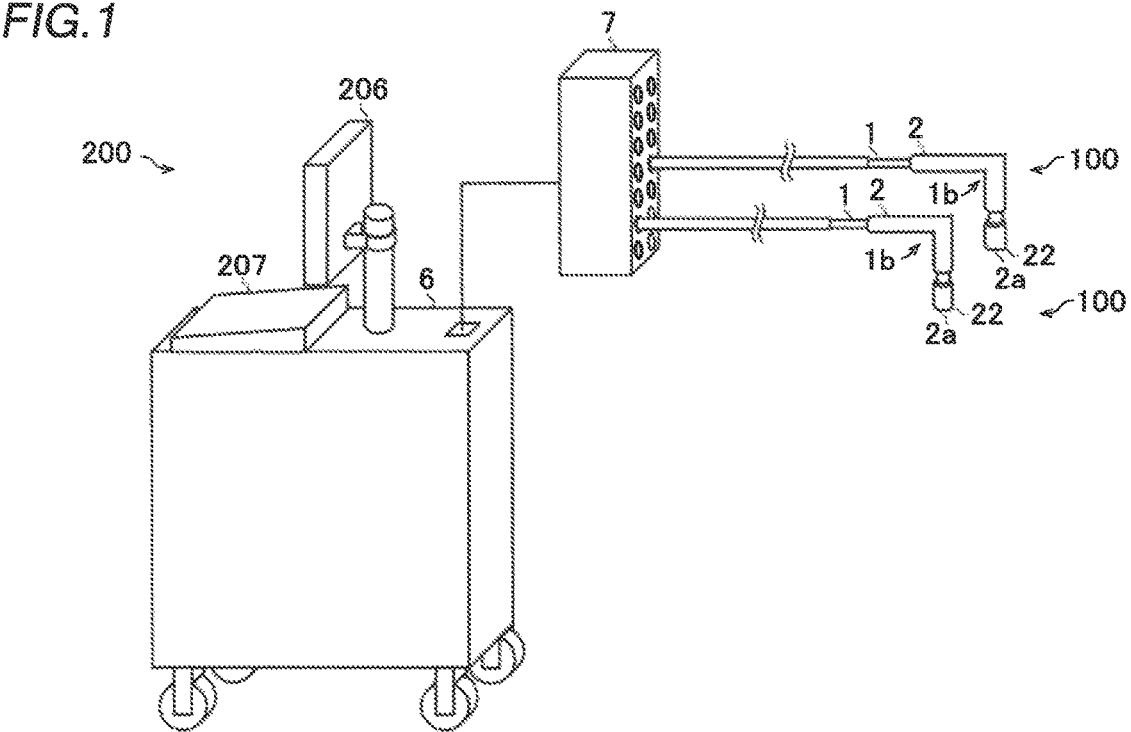
FIG. 1 is a perspective view schematically showing a brain function measuring device for preschoolers according to an embodiment.

An embodiment of the present invention is hereinafter described with reference to the drawings.
(Overall Configuration of Brain Function Measuring Device 200 for Preschoolers)

A brain function measuring device 200 for preschoolers including measurement probes 100 for preschoolers according to the embodiment is now described with reference to FIG. 1. A preschooler S is a child aged 0 to 6 years old before entering elementary school. The preschooler S is an example of a "subject" in the claims. The brain function measuring device 200 for preschoolers includes a plurality of measurement probes 100 for preschoolers, a holder 20, and a device main body 6.

Figure 2:
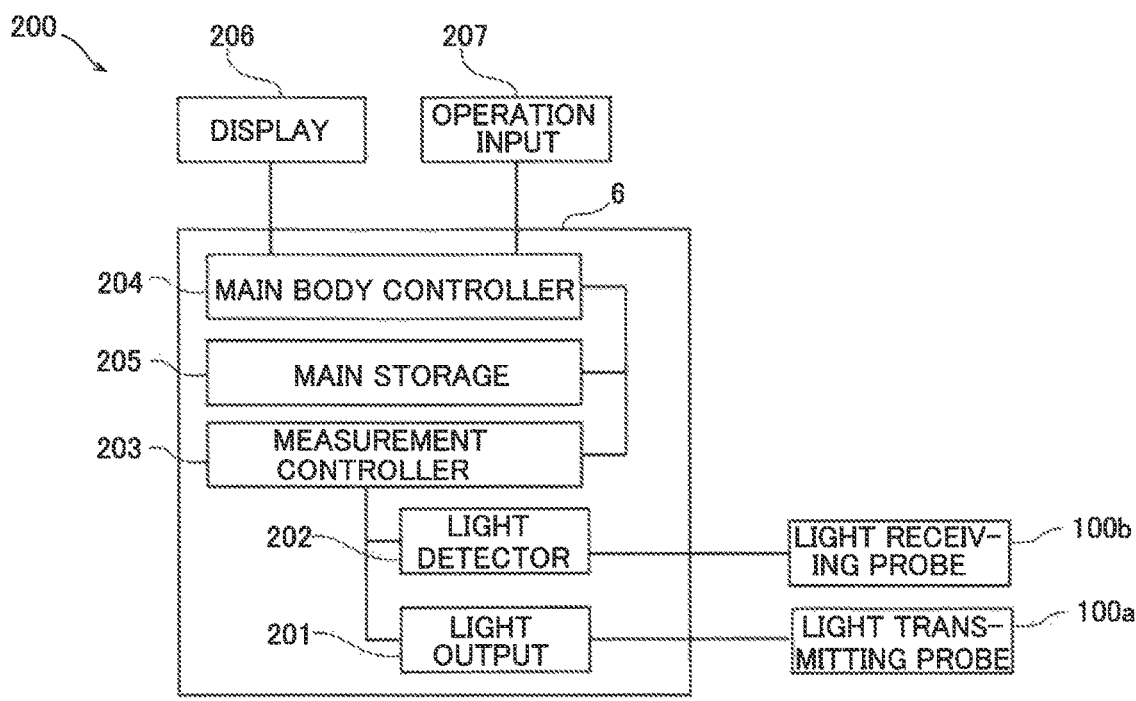
FIG. 2 is a block diagram showing the configuration of the brain function measuring device for preschoolers according to the embodiment.

As shown in FIG. 2, the device main body 6 includes a light output 201, a light detector 202, a measurement controller 203, a main body controller 204, a main storage 205, a display 206 configured to display measurement results, and an operation input 207.

The light output 201 is configured to output light to the measurement probes 100 for preschoolers. The light output 201 includes a semiconductor laser as a light source, for example. The light detector 202 is configured to detect light incident on the measurement probes 100 for preschoolers. The light detector 202 includes a photomultiplier tube as a detector, for example.

The measurement controller 203 is configured to control the operation of the light output 201 and the light detector 202. The main body controller 204 is configured to control the measurement operation of the entire brain function measuring device 200 for preschoolers by executing various programs. The main storage 205 is configured to store the various programs executed by the main body controller 204 and measurement data obtained as a result of measurement.
(Detailed Configuration of Measurement Probe for Preschoolers)

Figure 3:
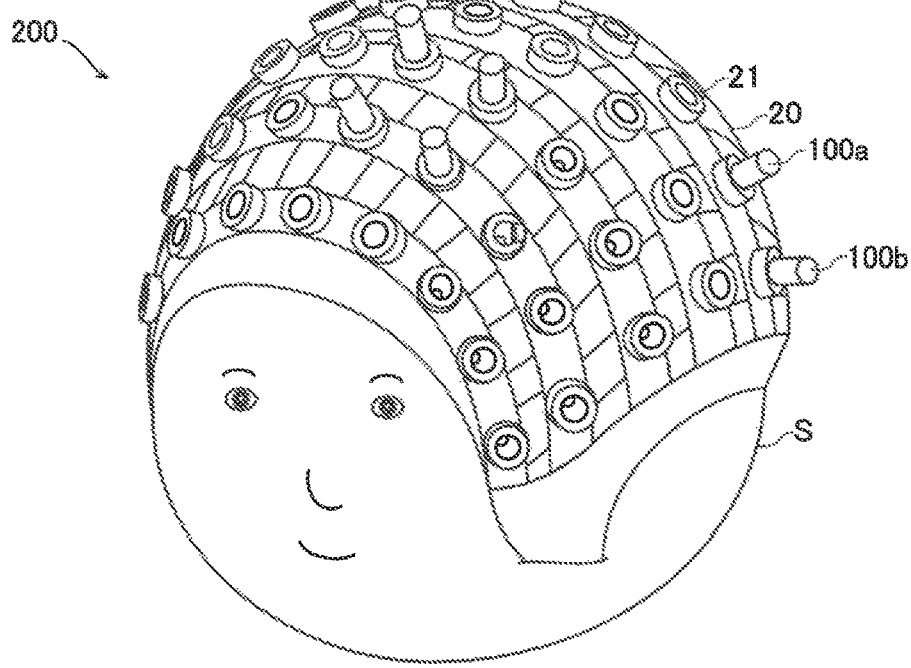
FIG. 3 is a diagram showing a state of attaching the brain function measuring device for preschoolers according to the embodiment.

As shown in FIG. 3, the plurality of measurement probes 100 for preschoolers are placed in a state in which their tips are in contact with the head of the preschooler S as the subject through the holder 20.

The measurement probes 100 for preschoolers include a plurality of light transmitting probes 100a and a plurality of light receiving probes 100b.

The light transmitting probes 100a are configured to irradiate the head of the preschooler S with light. The light receiving probes 100b are configured to receive light transmitted through the head of the preschooler S and reflected in the body of the preschooler S. The light transmitting probes 100a and the light receiving probes 100b have the same structure although their uses are different from each other. As an example, the light transmitting probes 100a and the light receiving probes 100b are alternately arranged such that the same type of probes are not adjacent to each other.

The light transmitting probes 100a are disposed in contact with the head surface of the preschooler S, and are configured to irradiate the head of the preschooler S with light in a near-infrared wavelength region. The light receiving probes 100b are disposed in contact with the head surface of the preschooler S, and are configured to allow the light reflected in the body of the preschooler S to enter thereinto and detect the light. Thus, the brain function measuring device 200 for preschoolers is configured to acquire the intensity of the light.

The brain function measuring device 200 for preschoolers radiates light in the near-infrared wavelength region from the light transmitting probes 100a disposed on the head surface of the preschooler S. Then, the brain function measuring device 200 for preschoolers acquires the intensity of the light (the amount of received light) by introducing the measurement light reflected in the subject into the light receiving probes 100b disposed on the head surface and causing the light receiving probes 100b to detect the light.

The brain function measuring device 200 for preschoolers is used for brain function measurement. An example of the brain function measurement is performed by irradiating the preschooler S with near-infrared light and detecting the reflected near-infrared light. This is a measurement method using the property that near-infrared light is absorbed by hemoglobin contained in blood that flows through blood vessels. When the brain is actively functioning, the hemoglobin content increases in order for the hemoglobin to supply required oxygen. Therefore, when the hemoglobin content in the brain increases in an activated region corresponding to the brain activity, the amount of measurement light absorption of hemoglobin increases. Accordingly, the brain function measuring device 200 for preschoolers can acquire variation of the hemoglobin content along with the brain activity based on the acquired intensity of the near-infrared light.

The brain function measuring device 200 for preschoolers can acquire two-dimensional distribution showing which region of the brain is active and how such a region functions by measuring a wide brain region at a plurality of points (measurement channels) with the plurality of light transmitting probes 100a and the plurality of light receiving probes 100b.

The holder 20 has a curved surface shape that matches the head shape. The holder 20 includes a number of adapters 21 arranged in a matrix at equal intervals along the surface shape of the head. The adapters 21 each have a cylindrical shape, and the measurement probes 100 (fibers 1) for preschoolers are inserted inside. The holder 20 shown in FIG. 3 is of an entire head type in which the measurement probes 100 for preschoolers can be placed on the entire head, and is formed in a helmet shape that covers an entire brain function measurement region of the head. The adapters 21 are circular holes that match the shapes of the measurement probes 100 for preschoolers. On the holder 20, the measurement probes 100 for preschoolers can be fixed to the adapters 21, respectively.

A user determines the arrangement of the measurement probes 100 for preschoolers into the adapters 21 according to a portion (such as a forehead, a top of the head, a temporal region of the head, or the entire head) of the head to be measured, and attaches the measurement probes 100 for preschoolers to the holder 20. When the measurement probes 100 for preschoolers are attached, the light transmitting probes 100a and the light receiving probes 100b are alternately arranged in the adapters 21 in each of row and column directions. Thus, a measurement channel (measurement point) is formed between the adjacent light transmitting probe 100a and light receiving probe 100b.

The holder 20 is fixed to the head of the preschooler S using a fixing belt (chin string), for example. Therefore, in the use state (wearing state), a contact pressure for maintaining the contact state and preventing the displacement is applied to each measurement probe 100 for preschoolers toward the head surface. A distance between the adapters 21 (a distance between the centers of the circles) is set to 25 mm or 20 mm, for example, which is smaller than that of a holder 20 for adults.

Figure 4:
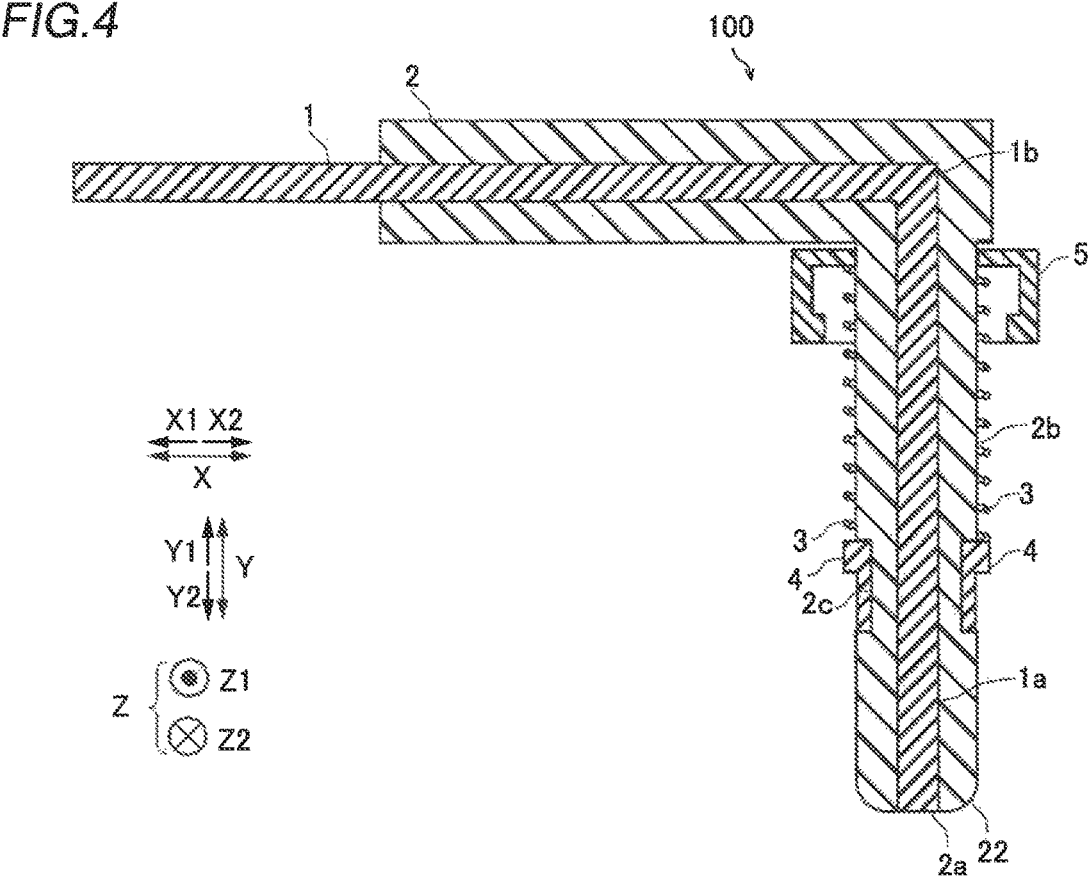
FIG. 4 is a schematic sectional view of a measurement probe for preschoolers according to the embodiment.

As shown in FIG. 4, the measurement probes 100 for preschoolers each include a fiber 1 and a holder 2 that covers the outer peripheral surface 1a of the fiber 1.

The measurement probe 100 for preschoolers is configured to radiate light from the fiber 1 to the head of the preschooler S. The fiber 1 is an optical fiber made of glass or plastic, for example. The fiber 1 has a bent portion 1b and is bent in an L shape. The tip surface of the tip of the fiber 1 that comes into contact with the head of the preschooler S is flat such that the preschooler S does not feel pain at the time of attaching measurement probe 100 for preschoolers.

The holder 2 is attached in such a manner as to cover the outer peripheral surface 1a of the tip of the fiber 1. The measurement probe 100 for preschoolers is attached to the holder 20 and is used, and thus rubber may come off when the outer peripheral surface 1a of the tip of the fiber 1 is covered with the rubber. Therefore, the holder 2 is made of a metal or resin that can be chamfered other than rubber while the strength of the fiber 1 is reinforced.

The holder 2 is configured to cover the L-shaped bent portion 1b of the fiber 1 and to extend to the tip of the fiber 1. The holder 2 is configured not to block light radiated from the fiber 1. Specifically, the holder 2 is configured to cover the annular outer peripheral surface of the fiber 1 in the radial direction without covering the tip surface of the fiber 1 that contacts the head of the preschooler S.

The fiber 1 does not protrude from the holder 2 to prevent damage of the fiber 1 and injury of the preschooler S due to direct contact of the fiber 1 with the head of the preschooler S.

A corner 22 of the tip 2a of the holder 2 that contacts the head of the preschooler S is chamfered. The chamfering is R-chamfering, for example.

The size of the R-chamfering is set so as not to affect the core of the fiber 1. For example, when the fiber 1 is 1 mm and the diameter of the measurement probe 100 for preschoolers is 4 mm, the size of the R-chamfering is set to 0.3 mm or more and 1.5 mm or less. The holder 2 can reduce a pressure applied to the head of the preschooler S by the measurement probe 100 for preschoolers due to the R-chamfering without being provided with a pad for buffering.

As shown in FIG. 4, the measurement probe 100 for preschoolers includes an urging member 3 and a stopper 4 attached to the outer peripheral surface 2b. The urging member 3 is disposed on the outer peripheral surface 2b of the holder 2. The urging member 3 is a coil spring, for example. The urging member 3 is in contact with the stopper 4. The stopper 4 is fixed to a recess 2c provided on the outer periphery of the holder 2.

The measurement probe 100 for preschoolers includes a cap 5 attached to the outer peripheral surface 2b. The cap 5 is used when the measurement probe 100 for preschoolers is attached and fixed to the adapter 21 of the holder 20.

Figure 5:
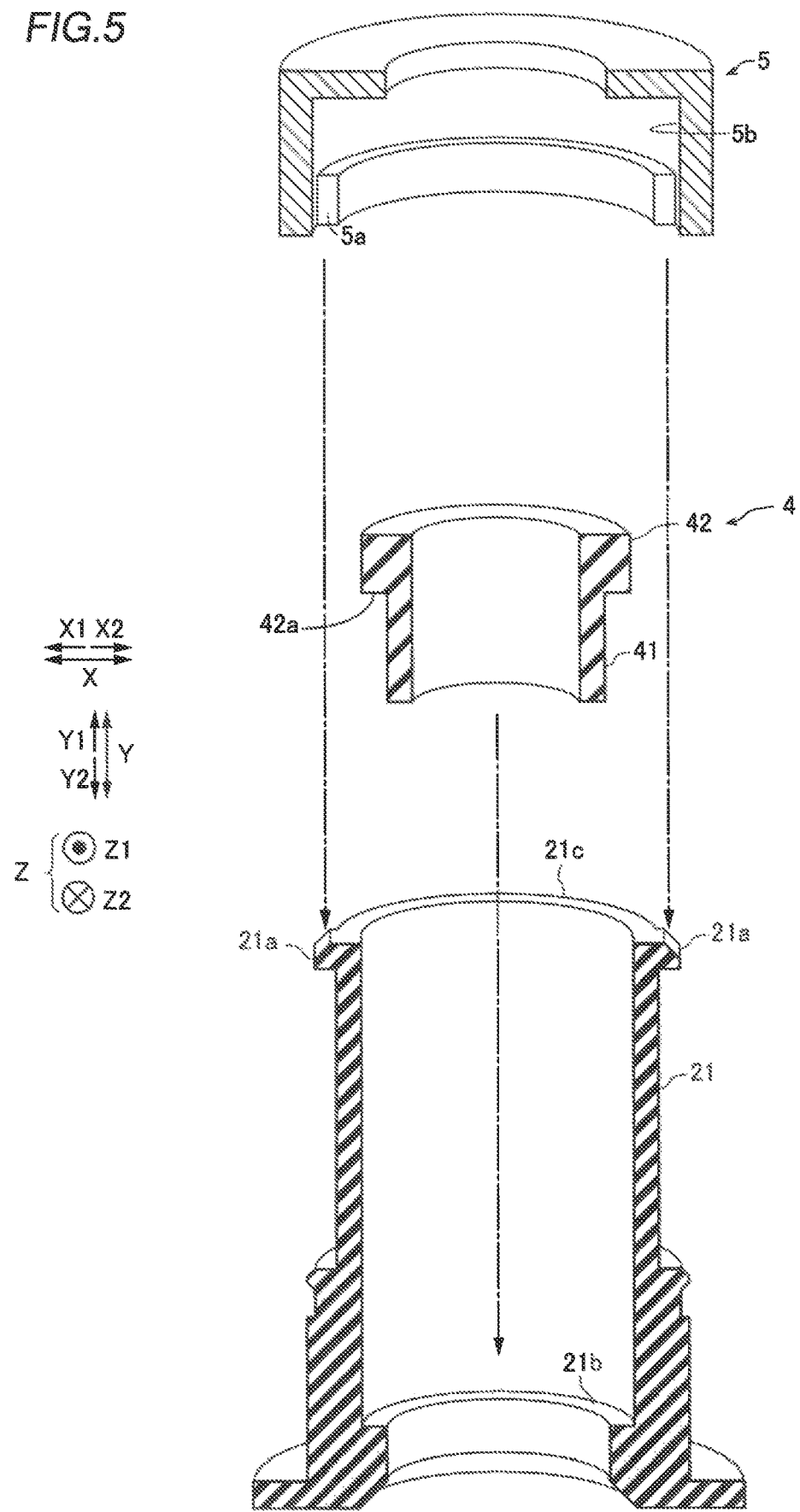
FIG. 5 is a diagram showing attachment of a cap to an adapter according to the embodiment.

FIG. 5 is a diagram for illustrating attachment of the stopper 4 and the cap 5 to the adapter 21, and the urging member 3 and the measurement probe 100 for preschoolers are omitted. As to the adapter 21, the stopper 4, and the cap 5 shown in FIG. 5, portions not shown in FIG. 5 and portions shown in FIG. 5 are symmetrically shaped.

The adapter 21 includes two first claws 21a on the outer peripheral surface 2b. The first claws 21a are provided only in one of an X direction and a Z direction. The adapter 21 has a mounting surface 21b inside. The stopper 4 has a cylindrical shape as a whole.

The measurement probe 100 (fiber 1) for preschoolers is inserted into the stopper 4. The stopper 4 includes a cylindrical portion 41 and a flange 42.

The cylindrical portion 41 has a cylindrical shape having a through-hole that extends in a Y direction. The flange 42 is provided on the outer peripheral surface of the Y1-direction end of the cylindrical portion 41. The flange 42 protrudes radially outward from the entire circumference of the cylindrical portion 41. The stopper 4 is arranged inside the adapter 21, and the bottom surface 42a of the flange 42 contacts the mounting surface 21b such that the movement is restricted. Thus, the stopper 4 is positioned with respect to the adapter 21.

The cap 5 engages with the adapter 21. The cap 5 includes a second claw 5a for attaching the adapter 21. The adapter 21 is attached to the cap 5 as described below. First, the cap 5 is inserted to the adapter 21 such that the second claw 5a of the cap 5 and a first notch 21c of the adapter 21 coincide. Then, the cap 5 is rotated such that the first claws 21a are caught in a U-shaped groove 5b (a portion provided on the inner peripheral surface of the cap 5 and a portion recessed radially outward) of the cap 5. Consequently, the adapter 21 engages with the cap 5. As a result, the measurement probe 100 for preschoolers is fixed to the cap 5 (holder 20).

Figure 6:
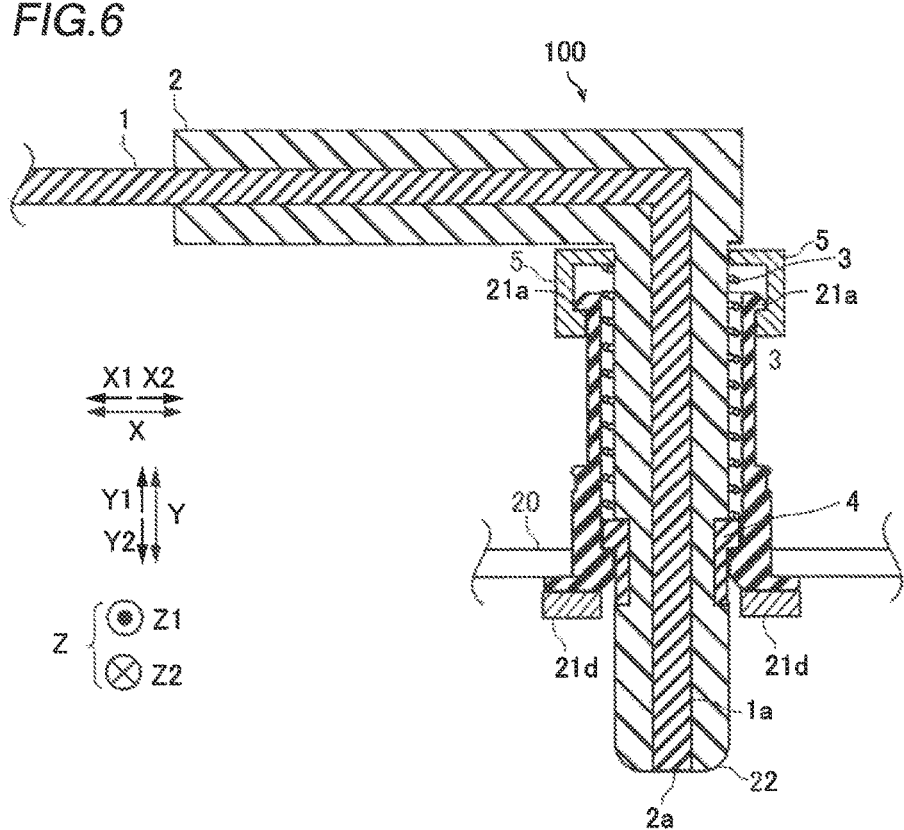
FIG. 6 is a diagram showing a state of attaching the measurement probe for preschoolers according to the embodiment to a holder.
Figure 7:
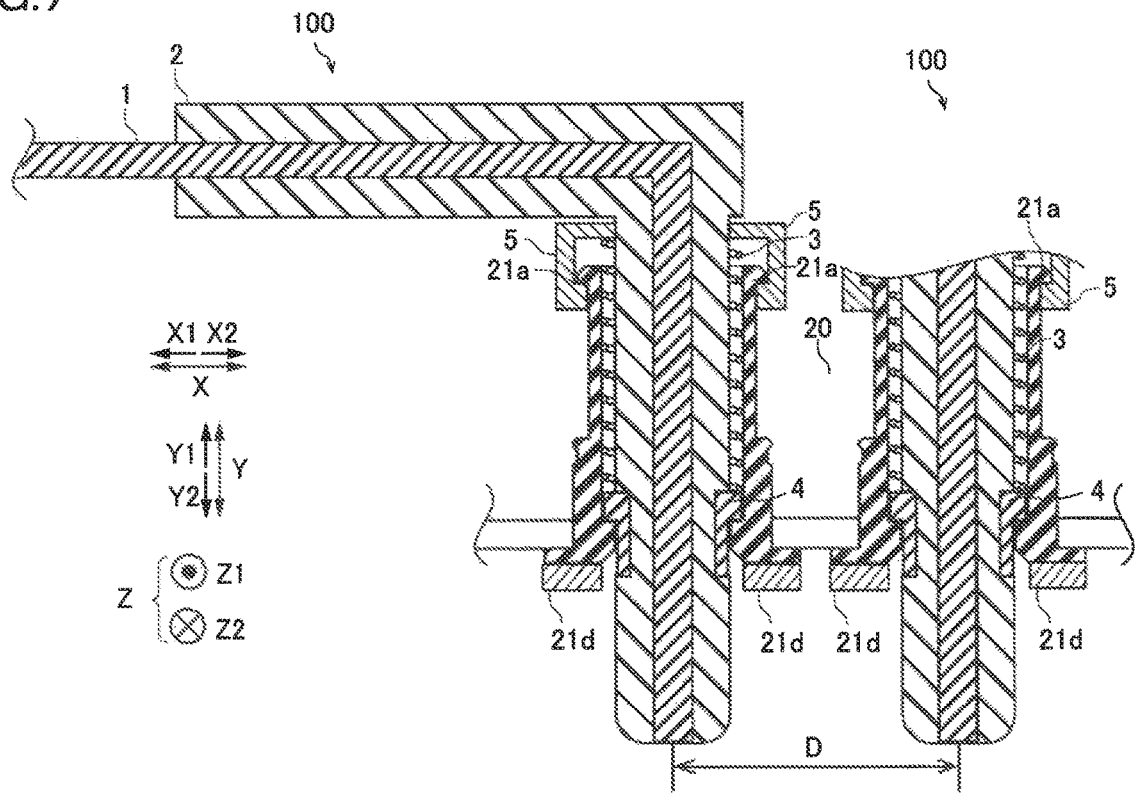
FIG. 7 is a diagram showing a state of attaching a plurality of measurement probes for preschoolers according to the embodiment to the holder.

As shown in FIG. 6, the measurement probe 100 for preschoolers is attached to the adapter 21 of the holder 20 by the cap 5 attached to the outer peripheral surface 2b. In this state, the holder 20 is attached to the preschooler S such that the measurement probe 100 for preschoolers contacts the head of the preschooler S. As shown in FIG. 6, a sponge 21d is attached to the tip of the adapter 21.

Figure 8:
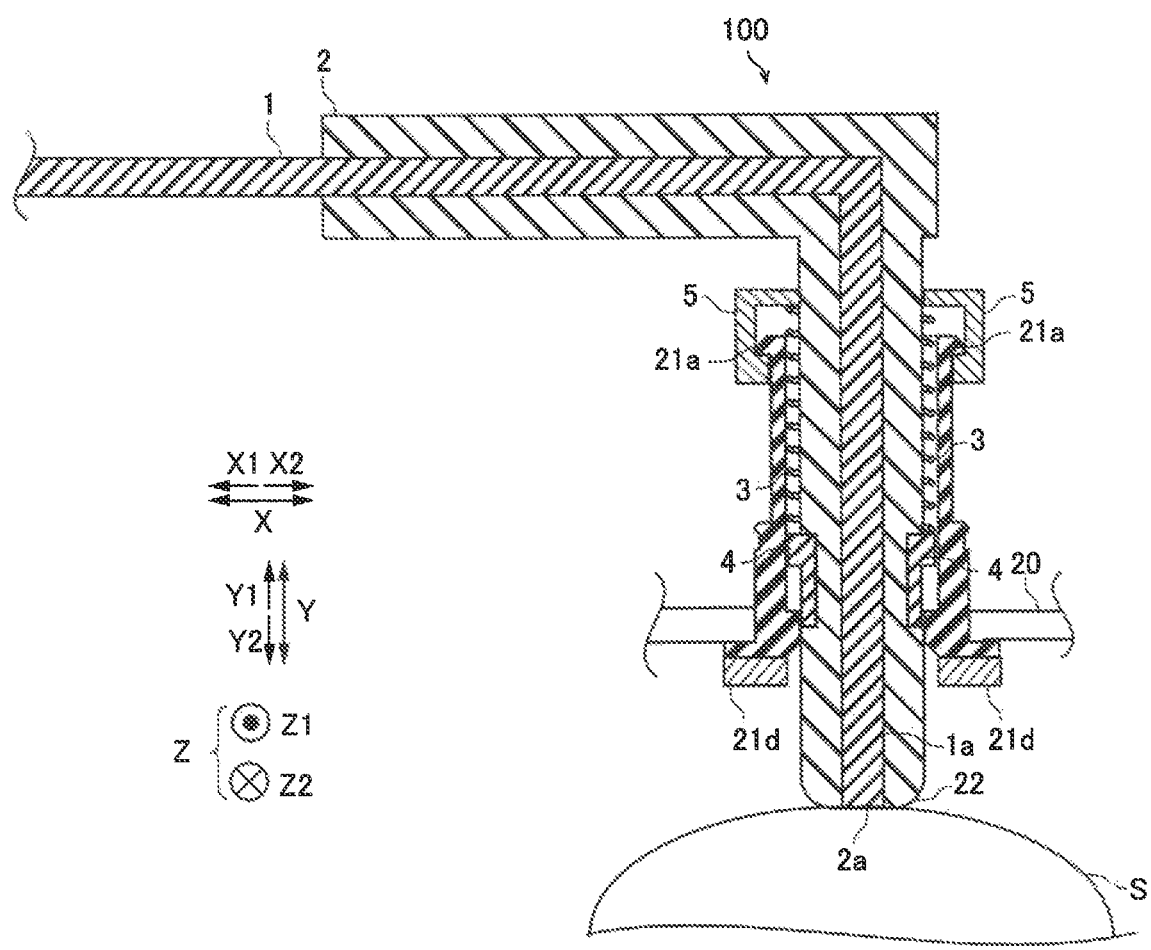
FIG. 8 is a diagram for illustrating movement of an urging member of the measurement probe for preschoolers according to the embodiment.

As shown in FIG. 8, when the tip of the measurement probe 100 for preschoolers is pressed against the head of the preschooler S, the fiber 1 and the holder 2 move relative to each other in an axial direction (Y1 direction). Therefore, the tip of the measurement probe 100 for preschoolers can stroke (move) in the axial direction (Y direction) according to the shape of the preschooler S. Moreover, the measurement probe 100 for preschoolers strokes in the axial direction such that the urging member 3 is pushed by the stopper 4, and thus the measurement probe 100 for preschoolers is urged. A state in which the tip 2a of the measurement probe 100 for preschoolers and the head surface contact each other is maintained by the urging force of the urging member 3.

As shown in FIG. 1, in this embodiment, the brain function measuring device 200 for preschoolers includes a probe relay terminal 7 between the measurement probes 100 for preschoolers and the device main body 6. A large number of measurement probe 100 terminals for preschoolers and measurement probe terminals for adults can be connected to the probe relay terminal 7. Therefore, the measurement probes 100 for preschoolers and the measurement probes for adults can be switched by switching the terminals to be inserted into the probe relay terminal 7. Moreover, the light transmitting probes 100a and the light receiving probes 100b can be switched depending on positions into the measurement probes 100 for preschooler are inserted.

Advantages of this Embodiment

According to this embodiment, the following advantages are obtained.

According to this embodiment, as described above, the measurement probes 100 for preschoolers disposed in contact with the head of the preschooler S and used for brain function measurement each include the fiber 1 configured to irradiate the head of the preschooler S as the subject with light and the holder 2 provided on the fiber 1 so as to cover the outer peripheral surface 1a of the tip of the fiber 1 and made of a metal or resin other than rubber, the tip surface of the tip of the fiber 1 that contacts the head of the preschooler S is flat, and the corner 22 of the tip surface of the holder 2 that contacts the head of the preschooler S is chamfered. Accordingly, the holder 2 is made of a metal or resin other than rubber, the tip surface of the tip of the fiber 1 that contacts the head of the preschooler S is flat, and the corner 22 of the tip surface, which contacts the head of the preschooler S, of the holder 2 that covers the outer peripheral surface 1a of the tip of the fiber 1 is chamfered such that the pressure applied to the head is reduced, and thus the pain at the time of attaching the measurement probe for preschoolers can be alleviated without providing rubber pads.

According to this embodiment, as described above, the corner 22 of the tip 2a of the holder 2 that contacts the head of the preschooler S is R-chamfered. Accordingly, the corner 22 of the tip surface of the holder 2 becomes round, and thus the pain produced when the preschooler S wears the measurement probes 100 for preschoolers can be effectively significantly reduced or prevented.

According to this embodiment, as described above, the holder 2 is made of a metal, and the corner 22 of the tip surface of the holder 2 made of a metal is R-chamfered. Accordingly, the strength of the fiber 1 can be improved by making the holder 2 of a metal.

According to this embodiment, as described above, the measurement probes 100 for preschoolers further includes the urging member 3 disposed on the outer peripheral surface 2b of the holder 2 and configured to urge the holder 2 toward the head of the preschooler S, and the stopper 4 configured to restrict movement of the urging member 3, and the outer peripheral surface 2b of the holder 2 includes the recess 2c configured to enable the stopper 4 to be fixed. Accordingly, the stopper 4 can be disposed at a predetermined position of the holder 2 by the recess 2c, and the stopper 4 restricts movement of the urging member 3 such that the measurement probes 100 for preschoolers can be urged toward the head of the preschooler S. Thus, a state in which the measurement probes 100 for preschoolers are in contact with the preschooler S can be maintained. In addition, even when the measurement probes 100 for preschoolers and the holder 20 are downsized for use in the preschooler S such that there is not enough space between the adapters 21 of the holder 20, the adhesion strength between the fiber 1 and the head of the preschooler S can be increased.

According to this embodiment, as described above, the fiber 1 is bent in an L shape, and the holder 2, the corner 22 of the tip surface of which is chamfered, is configured to cover the L-shaped bent portion 1b of the fiber 1 and to extend to the tip of the fiber 1. Accordingly, the bent portion 1b is covered with the holder 2 such that the fiber 1 can be kept bent, and thus the measurement probes 100 for preschoolers can be easily attached to the holder 20.

According to this embodiment, as described above, the brain function measuring device 200 for preschoolers includes the device main body 6, the plurality of measurement probes 100 for preschoolers electrically connected to the device main body 6, and the holder 20 attached with the plurality of measurement probes 100 for preschoolers and configured to maintain a state in which the plurality of measurement probes 100 for preschoolers are connected to the head of the preschooler S as the subject. Furthermore, the measurement probes 100 for preschoolers each include the fiber 1 configured to irradiate the head of the preschooler S as the subject with light, and the holder 2 provided on the fiber 1 so as to cover the outer peripheral surface 1a of the tip of the fiber 1 and made of a metal or resin other than rubber, the tip surface of the tip of the fiber 1 that contacts the head of the preschooler S is flat, and the corner 22 of the tip 2a of the holder 2 that contacts the head of the preschooler S is chamfered. Accordingly, similarly to the measurement probes 100 for preschoolers described above, it is possible to provide the brain function measuring device 200 for preschoolers that can reduce the pressure applied to the head of the preschooler S.

According to this embodiment, as described above, the brain function measuring device 200 for preschoolers further includes the probe relay terminal 7 provided between the measurement probes 100 for preschoolers and the device main body 6, connected with the plurality of measurement probes 100 for preschoolers and the device main body 6, and configured to transmit and receive a predetermined signal between the device main body 6 and the measurement probes 100 for preschoolers. Accordingly, the measurement probes 100 for preschoolers and the measurement probes for adults can be switched simply by switching the measurement probes connected to the probe relay terminal 7. That is, the measurement probes 100 for preschoolers and the measurement probes for adults can be easily switched.

Modified Examples

The embodiment disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while the present invention is applied to the measuring device that performs brain function measurement by irradiating the subject with light using the measurement probes including the fibers in the aforementioned embodiment, the present invention is not limited to this. The present invention may alternatively be applied to a brain function measuring device for preschoolers other than the optical measuring device as long as the same is a brain function measuring device for preschoolers including measurement probes for preschoolers. While the corner of the tip surface of the holder that contacts the head of the subject is R-chamfered in the aforementioned embodiment, the present invention is not limited to this. For example, the corner of the tip surface of the holder that contacts the head of the subject may alternatively be C-chamfered.

While the measurement probes for preschoolers are each fixed to the holder by the cap in the aforementioned embodiment, the present invention is not limited to this. For example, an engaging member may alternatively be provided and attached to the holder.

While the measurement probes for preschoolers are L-shaped in the aforementioned embodiment, the present invention is not limited to this. For example, the measurement probes for preschoolers each may not include the bent portion so as to be linear.

While the probe relay terminal is provided between the measurement probes for preschoolers and the device main body in the aforementioned embodiment, the present invention is not limited to this. For example, the measurement probes for preschoolers and the device main body may alternatively be directly connected to each other without providing the probe relay terminal.

Aspects

It will be appreciated by those skilled in the art that the exemplary embodiments described above are specific examples of the following aspects.

(Item 1)

A measurement probe for preschoolers for brain function measurement disposed in contact with a head of a subject, the measurement probe for preschoolers comprising:

a fiber configured to irradiate the head of the subject with light; and a holder provided on the fiber so as to cover an outer peripheral surface of a tip of the fiber, the holder being made of a metal or resin other than rubber; wherein a tip surface of the tip of the fiber that contacts the head of the subject is flat; and a corner of a tip surface of the holder that contacts the head of the subject is chamfered.

(Item 2)

The measurement probe for preschoolers according to item 1, wherein the corner of the tip surface of the holder that contacts the head of the subject is R-chamfered.

(Item 3)

The measurement probe for preschoolers according to item 2, wherein the holder is made of the metal; and the corner of the tip surface of the holder made of the metal is R-chamfered.

(Item 4)

The measurement probe for preschoolers according to item 1, further comprising:

an urging member disposed on an outer peripheral surface of the holder and configured to urge the holder toward the head of the subject; and a stopper configured to restrict movement of the urging member; wherein the outer peripheral surface of the holder includes a recess configured to enable the stopper to be fixed.

(Item 5)

The measurement probe for preschoolers according to item 1, wherein the fiber is bent in an L shape; and the holder, the corner of the tip surface of which is chamfered, is configured to cover an L-shaped bent portion of the fiber and to extend to the tip of the fiber.

(Item 6)

A brain function measuring device for preschoolers, comprising:

a device main body;

a plurality of measurement probes for preschoolers electrically connected to the device main body; and a holder attached with the plurality of measurement probes for preschoolers, the holder being configured to maintain a state in which the plurality of measurement probes for preschoolers are connected to a head of a subject; wherein the plurality of measurement probes for preschoolers each include:

a fiber configured to irradiate the head of the subject with light; and a holder provided on the fiber so as to cover an outer peripheral surface of a tip of the fiber, the holder being made of a metal or resin other than rubber;

a tip surface of the tip of the fiber that contacts the head of the subject is flat; and a corner of a tip surface of the holder that contacts the head of the subject is chamfered.

(Item 7)

The brain function measuring device for preschoolers according to item 6, further comprising a probe relay terminal provided between the plurality of measurement probes for preschoolers and the device main body, the probe relay terminal being connected with the plurality of measurement probes for preschoolers and the device main body, the probe relay terminal being configured to transmit and receive a predetermined signal between the device main body and the plurality of measurement probes for preschoolers.

What is claimed is:

1. A measurement probe for preschoolers for brain function measurement configured to be disposed in contact with a head of a subject, the measurement probe for preschoolers comprising:

a fiber configured to irradiate the head of the subject with light; and a fiber holder provided on the fiber so as to cover an outer peripheral surface of a tip of the fiber, the fiber holder being made of a metal; wherein a tip surface of the tip of the fiber is configured to contact the head of the subject is flat;

a corner of a tip surface of the fiber holder is configured to contact the head of the subject is chamfered;

the fiber holder is configured to be composed of a single member that covers the outer peripheral surface of the fiber at least from the portion corresponding to an upper surface of a probe holder attached with the measurement probe to the tip surface of the tip of the fiber; and the corner of the tip surface of the fiber holder made of the metal is chamfered.

2. The measurement probe for preschoolers according to claim 1, wherein the corner of the tip surface of the fiber holder is configured to contact the head of the subject is R-chamfered.

3. The measurement probe for preschoolers according to claim 1, further comprising:

an urging member disposed on an outer peripheral surface of the fiber holder and configured to urge the fiber holder toward the head of the subject; and a stopper configured to restrict movement of the urging member; wherein the outer peripheral surface of the fiber holder includes a recess configured to enable the stopper to be fixed.

4. The measurement probe for preschoolers according to claim 1, wherein the fiber is bent in an L shape; and the fiber holder is configured to cover an L-shaped bent portion of the fiber and to extend to the tip of the fiber.

5. A brain function measuring device for preschoolers, comprising:

a device main body;

a plurality of measurement probes for preschoolers electrically connected to the device main body; and a probe holder attached with the plurality of measurement probes for preschoolers, the probe holder being configured to maintain a state in which the plurality of measurement probes for preschoolers are configured to be connected to a head of a subject; wherein the plurality of measurement probes for preschoolers each include:

a fiber configured to irradiate the head of the subject with light; and a fiber holder provided on the fiber so as to cover an outer peripheral surface of a tip of the fiber, the fiber holder being made of a metal;

a tip surface of the tip of the fiber is configured to contact the head of the subject is flat;

a corner of a tip surface of the fiber holder is configured to contact the head of the subject is chamfered;

the fiber holder is configured to be composed of a single member that covers the outer peripheral surface of the fiber at least from the portion corresponding to an upper surface of the probe holder attached with the measurement probe to the tip surface of the tip of the fiber; and the corner of the tip surface of the fiber holder made of the metal is chamfered.

6. The brain function measuring device for preschoolers according to claim 5, further comprising a probe relay terminal provided between the plurality of measurement probes for preschoolers and the device main body, the probe relay terminal being connected with the plurality of measurement probes for preschoolers and the device main body, the probe relay terminal being configured to transmit and receive a predetermined signal between the device main body and the plurality of measurement probes for preschoolers.

* * * * *